United States Patent
Schwendeman et al.

(10) Patent No.: US 10,369,106 B2
(45) Date of Patent: Aug. 6, 2019

(54) EFFICIENT AQUEOUS ENCAPSULATION AND CONTROLLED RELEASE OF BIOACTIVE AGENTS

(71) Applicant: The Regents of The University of Michigan, Ann Arbor, MI (US)

(72) Inventors: Steven P. Schwendeman, Superior Township, MI (US); Ronak B. Shah, Ann Arbor, MI (US); Morgan B. Giles, Ann Arbor, MI (US); Rae Sung Chang, Ann Arbor, MI (US); Anna A. Schwendeman, Superior Township, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 14/537,716

(22) Filed: Nov. 10, 2014

(65) Prior Publication Data
US 2015/0164805 A1 Jun. 18, 2015

Related U.S. Application Data

(60) Provisional application No. 61/901,952, filed on Nov. 8, 2013.

(51) Int. Cl.
| | |
|---|---|
| *A61K 9/16* | (2006.01) |
| *A61K 47/30* | (2006.01) |
| *A61K 38/18* | (2006.01) |
| *A61K 38/22* | (2006.01) |
| *A61K 38/47* | (2006.01) |

(52) U.S. Cl.
CPC ........ *A61K 9/1652* (2013.01); *A61K 9/1611* (2013.01); *A61K 9/1623* (2013.01); *A61K 9/1647* (2013.01); *A61K 9/1694* (2013.01); *A61K 38/1825* (2013.01); *A61K 38/1866* (2013.01); *A61K 38/2264* (2013.01); *A61K 38/47* (2013.01); *C12Y 302/01017* (2013.01)

(58) Field of Classification Search
None
See application file for complete search history.

(56) References Cited

U.S. PATENT DOCUMENTS

| | | |
|---|---|---|
| 8,017,155 B2 | 9/2011 | Schwendeman et al. |
| 2002/0009493 A1 | 1/2002 | Schwendeman et al. |
| 2003/0026844 A1 | 2/2003 | Lee et al. |
| 2007/0081976 A1 | 4/2007 | Cohen et al. |
| 2012/0288537 A1 | 11/2012 | Schwendeman et al. |

FOREIGN PATENT DOCUMENTS

WO   WO 2011088229 A2 *   7/2011   ....... A61K 47/48015

OTHER PUBLICATIONS

Lee et al., Biomaterials, 2007, 28, 2754-2762.*
International Search Report and Written Opinion of the International Searching Authority dated Feb. 26, 2015 for PCT Application No. PCT/US2014/064872.

* cited by examiner

*Primary Examiner* — Abigail Vanhorn
(74) *Attorney, Agent, or Firm* — Marshall, Gerstein & Borun LLP

(57) ABSTRACT

A drug delivery system comprises a porous, self-healing biodegradable polymer matrix having a ionic, charged, biopolymer and a pH modifying species disposed within the pores. An ionic macromolecule having the opposite charge binds the biopolymer and forms a nonsoluble polyelectrolyte complex. The molecular weight of the biopolymer, the self healing polymer matrix, the concentration of pore forming agent and the concentration of the pH modifying species are selected for optimal binding and release of the macromolecule.

10 Claims, 6 Drawing Sheets

EFFICIENT AQUEOUS ENCAPSULATION AND CONTROLLED RELEASE OF BIOACTIVE AGENTS

RELATED APPLICATIONS

This application claims the benefit of priority to U.S. Provisional Patent Application No. 61/901,952, filed Nov. 8, 2013, the contents of which are hereby incorporated by reference in its entirety.

GOVERNMENT RIGHTS

This invention was made with U.S. Government support under grant numbers NIH HL 68345, NIH EB 08873 awarded by the National Institutes of Health. The U.S. Government has certain rights in the invention.

FIELD

The present technology relates to a delivery system with high encapsulation efficiency for an agent such as a biomolecule.

INTRODUCTION

Injectable, biodegradable polymeric particles, such as microspheres, provide a means to deliver and control the release of molecules such as drugs, proteins, peptides and vaccine antigens. Once injected, the biodegradable polymeric particles can release the molecule over the course of hours, days or even extended periods such as weeks or months, thus eliminating the need for daily injections, and thereby improving patient acceptance and compliance. Controlled release of a protein antigen can reduce the number of doses in an immunization schedule and optimize the desired immune response by selectively targeting the antigen to the targeted antigen presenting cells.

An array of biodegradable polymers have been used for the microencapsulation and delivery of macromolecules. For example copolymers of lactic acid and glycolic acid (PLGA) are biodegradable and biocompatible, and have been used in pharmaceutical products and medical devices that have been approved by the U.S. Food and Drug Administration. PLGA polymer systems are presently used in commercially available, controlled-release delivery systems for peptides including leuprolide acetate (Lupron Depot™), octreotide acetate (Sandostatin LAR™), goserelin acetate (Zoladex™ implant).

Microspheres are of intense interest for controlled-release, injectable depots capable of the slow, complete release in vivo of proteins in their native (active) state because they are capable of sequestering these macromolecules and protecting them from enzymatic or other degradation before they are released. Nevertheless, significant obstacles have been encountered. Of concern is the stability of proteins and peptides during encapsulation. Methods for encapsulating macromolecules in biodegradable polymers can involve harsh processing conditions, including exposure to organic solvents, excess heat, and homogenization methods such as mixing, sonication and high-speed agitation. These methods alone or in combination can denature and/or destabilize proteins and other macromolecules. Drying and micronization of a macromolecule prior to encapsulation may further destabilize the macromolecule.

Hydrophilic macromolecules, including many proteins, cannot readily diffuse through a hydrophobic polymer phase of many biodegradable polymers such as PLGA. The release of encapsulated protein drugs from a PLGA matrix, therefore, requires the macromolecules to diffuse through water-filled pores or channels. As a result, protein release from PLGA microspheres often exhibits tri-phasic behavior. In the first phase, protein on the surface or having immediate access to the surface of the microspheres (i.e., in open pores) is released rapidly, providing an initial burst release. Second, a time lag occurs, as the protein within the interior of the microsphere cannot diffuse through the polymer phase. Third, a continuous release of protein occurs due to polymer erosion that causes more pores and channels to be formed allowing protein to be released from previously isolated pores or chambers within the microsphere.

Encapsulation methods using preformed microspheres comprising self-healing polymers have been developed for peptides, proteins, DNA, siRNA, and other macromolecules (U.S. Pat. No. 8,017,155, Schwendeman et al. hereby incorporated by reference in its entirety). The macromolecule is loaded into a preformed, porous microsphere, preferably having an interconnected pore network having access to the external aqueous solution. Loading is performed in an aqueous solution of the macromolecules at a temperature that is below the glass transition temperature ($T_g$) so that the macromolecule is taken up into the pores of the polymer. Next, the temperature is raised above the $T_g$ so that the polymer pores close (heal), encapsulating the macromolecule. PLGA has a hydrated glass transition temperature well below common PLGA healing temperatures of 37-43° C., a temperature range at which many proteins are stable in aqueous solutions with or without protein stabilizers for appreciable lengths of time to allow pore healing (closure). However, plasticizers have also been added to PLGA to reduce the healing temperature to 37° C. Alternatively, other methods besides temperature change can be used to close the pores. For example, exposure to a solvent, such as alcohol vapor, can be used to facilitate pore closure (self-healing) of the polymer matrix. Using this methodology, loading of about 10% w/w of active protein agent to PLGA can be achieved.

Passive encapsulation methods rely on equilibration of the peptide or protein to be delivered between the solution outside the polymer phase or microsphere, and the aqueous pores within the microsphere. Passive encapsulation typically requires high concentrations of the macromolecule (>50-100 mg/mL) in order to achieve adequate loading. This elevated concentration requirement could prohibit encapsulation of macromolecules with moderate to low solubility. In addition, passive encapsulation generally results in low encapsulation efficiency, leaving most of the macromolecule in the loading solution after encapsulation. This may result in significant losses of biologic macromolecules such as proteins during encapsulation. Since recombinant proteins or those isolated from biological sources are expensive to produce, this can add considerable cost to the encapsulation process. The macromolecule solution could potentially be reused multiple times to avoid wasting the macromolecule. However some macromolecules are unstable and are not amenable to this process.

Some of these problems have been circumvented by the advances disclosed in U.S. Patent Application Publication US 2012-0288537 (hereby incorporated by reference in its entirety), including an ionic affinity trap disposed within the microsphere. The described ionic affinity trap can comprise a metal salt such as aluminum hydroxide, aluminum phosphate, potassium phosphate, magnesium carbonate, calcium phosphate or an ionomer gel. Alternatively, the ionic affinity trap can comprise ionized end groups of the polymer, for example, in the case of PLGA the carboxylate groups of the polymer. The agent to be delivered can comprise a biomolecule, a drug, or an antigen, and include proteins, peptides, proteoglycans, lipoproteins, and nucleic acids. The agent to be delivered can be sorbed to the ionic affinity trap enabling the delivery system to provide higher loading and incorporate a higher level of bioactive agent in the delivery system. Compared to previous delivery systems, these delivery systems achieved elevated loading (>1% w/w) from protein concentrations (<1 mg/ml). Although these advances showed improved encapsulation efficiency of protein antigens or loading for bioactive peptides, they did not show efficient loading (e.g., encapsulation efficiency >60%) of pharmaceutical peptides or proteins, or achieve elevated protein loading >3% w/w, which is necessary for certain polypeptide depot formulations (e.g., Bydureon and Lupron Depot, marketed products that have loading ≥5% w/w).

It would therefore be desirable to provide an microsphere-based, or similar, controlled delivery system for proteins and other macromolecules, which a) does not expose the active agent to solvents or other harsh conditions during manufacture, b) is capable of loading from aqueous solutions of the active agent at low concentrations, and c) achieves both high loading and high encapsulation efficiency. Additionally, the delivery system would deliver the protein or other macromolecule in its active form over an extended period of time.

SUMMARY OF THE INVENTION

One aspect of the present invention provides a drug delivery system comprising a porous, self-healing biodegradable polymer matrix and a biopolymer and a solid pH-modifying species both disposed within the pores of the polymer matrix. An ionic macromolecule is bound to the biopolymer, and together, they form a non-soluble polyelectrolyte complex, which hinders translational motion of the macromolecule.

Another aspect of the invention provides a delivery system comprising self-healing microspheres, comprising porous poly(lactic-co-glycolic acid) (PLGA), or an equivalent self-healing polymer, and having an interconnected porous network that is connected to the outer surface of the microsphere. Disposed within the interior porous network is a sulfated glycosamino-glycan, and bound to the sulfated glycosamino-glycan is an active protein agent that, together with the glycosamino-glycan, forms a polyelecrolyte with restricted translational motion.

Another aspect of the invention provides a method for making a drug delivery system for a macromolecule by first preparing self-healing porous microspheres having an interconnected pore network connected to the outer surface of the microsphere. The microspheres comprise a self-healing polymer, at least one pore forming agent, a solid pH modifying species, and a biopolymer that is disposed within the interconnected pore network of the microspheres. Next a macromolecule is loaded into the interconnected porous network of the microspheres by incubating the microspheres in an aqueous solution of the macromolecule and allowing the macromolecule to enter the porous network and penetrate deep into the interior of microsphere. The macromolecule is allowed to bind to the biopolymer disposed within the interior of the microsphere and form a polyelectrolyte complex before the biopolymer substantially diffuses out of the polymer matrix, and, finally, the pores connected to the outer surface of the microspheres are closed, thereby encapsulating the macromolecule. The self-healing polymer, the molecular weight of the biopolymer, concentration of pore forming agent and the concentration of the pH modifying species are selected for optimal binding and release of the macromolecule.

In another aspect, the present invention provides a drug delivery system comprising porous, biodegradable polymer microspheres having an interior space, a biopolymer disposed within the interior space of the microsphere, and an active macromolecule agent to be delivered bound to the biopolymer.

In another aspect, the invention provides a delivery system comprising self-healing, porous poly(lactic-co-glycolic acid) (PLGA) microspheres having an interior space. At least a portion of the interior space is a percolating porous network connected to the outer surface of the microsphere before healing (or closing the surface pores). Disposed within the interior porous network is a sulfated glycosamino-glycan, and bound to the sulfated glycosaminoglycan is an active protein agent to be delivered.

In another aspect, the invention provides a method for making a drug delivery system for a macromolecule by first preparing porous microspheres having an interior space, at least a portion of which is a percolating pore network connected to the outer surface of the microsphere. The microspheres comprise poly(lactic-co-glycolic acid), at least one pore forming agent, a pH modifying species, and a biopolymer that is disposed within the interior space of the microspheres. Next a macromolecule is loaded into the porous microspheres by incubating the microspheres in an aqueous solution of the macromolecule and allowing the macromolecule to enter the porous network of the microspheres and penetrate deep into the interior space of microsphere. The macromolecule is allowed to bind to the biopolymer disposed within the interior of the microsphere, and, finally, the pores connected to the outer surface of the microspheres are closed, thereby encapsulating the macromolecule. The molecular weight of the biopolymer, the poly(lactic-co-glycolic acid) concentration, concentration of pore forming agent and the concentration of the pH modifying species are selected for optimal delivery of the macromolecule.

DETAILED DESCRIPTION

Figure 1:
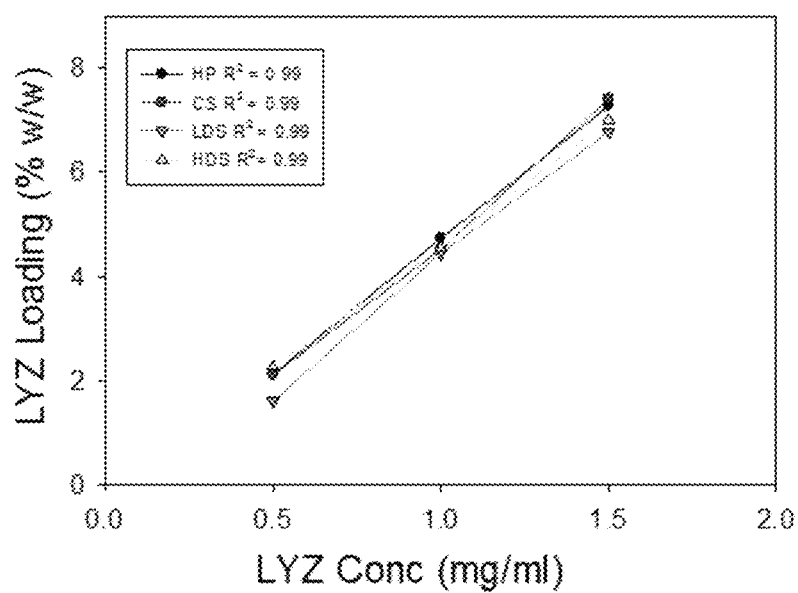
FIG. 1 is a graphical representation showing the fit of the w/w LYZ loading of optimal biopolymer-PLGA microspheres as a function of the LYZ loading concentration. Theoretical content of biopolymers, trehalose and MgCO3 was ~4, 3 and 3% w/w, respectively, in the formulations, in accordance with the present invention.

The present invention is directed to microsphere-based delivery systems for pharmaceutically active agents such as proteins and other large molecules (biomacromolecules). The system comprises preformed, porous microspheres, and one or more biopolymers within the microspheres that bind, sequester, and stabilize the agent to be delivered. In some embodiments the biopolymers enhance the biological effect(s) of the protein by acting as co-factors. In other embodiments the biopolymers stabilize the protein by immobilizing it much as physiological extracellular matrix stabilizes the structure of growth factors upon binding.

Natural and synthetic polymers such as poly(lactides), poly(glycolides), poly(lactide-co-glycolides), poly(lactic acid)s, poly(glycolic acid)s, poly(lactic acid-co-glycolic acid)s, polycaprolactone, poly(hydroxymethyl glycolide-co-lactide), polycarbonates, polyesteramides, polyanhydrides, poly(amino acids), polyorthoesters, polycyanoacrylates, poly(p-dioxanone), poly(alkylene oxalate)s, biodegradable polyurethanes, homopolymers, copolymers, and blends of these and other polymers have been used to form a porous polymer matrix. Such porous polymer matrices are widely used in medical devices and formulations for drug delivery, and are appropriate for various embodiments of the present invention. Among these polymers, poly(lactic-co-glycolic acid) (PLGA)-based polymers possess highly desirable qualities for drug delivery such as biodegradability and biocompatibility. PLGA polymers have been used extensively in microspheres, millicylindrical rods, coatings and various other devices, and their rates of degradation and biocompatibility are well understood.

In one embodiment of the invention PLGA is formulated with pore forming agents such as sugars, salts, or any other porosigen to form a biodegradable polymer matrix having pores. Suitable sugars include monosaccharides, disaccharides, oligosaccharides, and polysaccharides. An example is trehalose, a disaccharide containing two glucose units. The level of porosogen is selected for forming a suitable pore structure. In various embodiments, the porosogen is provided in the recipe at a level of 1-10%, 1-6%, 1-5%, 2-10%, 2-6%, or 2-5%, for example at about 3% or about 4% by weight of the biodegradable polymer. In one embodiment of the invention, the polymer matrix forms microspheres, and the type and amount of the pore forming agent is selected to form an interconnected pore network within the interior of the microsphere that connects to the surface of the microsphere. This porous network will allow an active biomacromolecule agent to penetrate deep into the interior of the microsphere during encapsulation, and to diffuse out of the microsphere through the pore network at an optimal rate during subsequent controlled release.

One major drawback to using PLGA polymers is that an acidic microenvironment may develop within the interior porous structure of the microsphere, due to the build-up of acidic degradation products of the polymer during polymer erosion and extended drug delivery. This problem has been largely overcome by incorporation of basic additives or other pH-modifying species such as metal salts into the polymer phase during formation of microspheres. Basic additives appropriate for use in various embodiments of the present invention include magnesium carbonate, magnesium hydroxide, magnesium oxide, magnesium trisilicate, zinc carbonate, zinc hydroxide, zinc phosphate, aluminum hydroxide, basic aluminum carbonate, dihydroxyaluminum sodium carbonate, dihydroxyaluminum aminoacetate, calcium phosphate, and calcium hydroxide. In one embodiment of the invention a pH modulator is used that has a low aqueous solubility and is a solid within the polymer matrix. In various embodiments, the pH modulator is used at a level of about 1% to about 7% by weight of the biodegradable polymer.

In one embodiment of the invention, microspheres are prepared using a double water-oil-water (W/O/W) emulsion of poly(lactic-co-glycolic acid) (PLGA), with $MgCO_3$ or $ZnCO_3$ as a pH modulator, trehalose as a pore forming agent, and in addition, a biopolymer is added during microsphere formation and is incorporated into the interior of the microsphere.

In one embodiment of the invention biopolymers are selected that act as binding agents for the active macromolecular agents to be delivered in order to enhance the efficiency of microencapsulation of the agent in PLGA microspheres. The macromolecular agent to be encapsulated may be a peptide, a protein, a nucleic acid, DNA, siRNA, or other large molecule. In one embodiment the macromolecular agent is a protein. In some embodiments the molecular weight of the macromolecular agent is >1000 kDa.

Desirable characteristics of biopolymers appropriate for use in delivery systems include the ability to: absorb the macromolecular agent of interest from aqueous solution; stabilize the bound macromolecule agent; release the bound macromolecular agent when the PLGA pores open; and optionally, provide a synergistic therapeutic effect along with the agent of interest.

Suitable biopolymers include hyaluronic acid, chondroitin sulfate, heparin, chitosan and dextran sulfate. These biopolymers are members of the glycosamino-glycan (GAG) family, or have similar structural moieties (e.g. dextran sulfate). GAGs are polysaccharides that constitute a major portion of the extra cellular matrix, and are therefore biocompatible and non-immunogenic. They are linear, generally sulfated, negatively charged polysaccharides with molecular weights in 10-100 kDa range. Non-sulfated GAGs include hyaluronic acid (HA); sulfated GAGs include chondroitin sulfate (CS), dextran sulfate (DS), ketran sulfate (KS), heparin and heparin sulfate (HP). In various embodiments, the biopolymer is used at a level of at least 0.5%, at least 1%, at least 1.5%, at least 2%, or at least 2.5% by weight of the biodegradable polymer, and at a level below 10%, below 7.5%, below 6%, below 5%, and below 4%, wherein all percentages are by weight of the biodegradable polymer.

In some embodiments of the invention, glycosoaminoglycans incorporated into the delivery system bind and immobilize the protein or other macromolecular agent to be delivered by forming a polyelectrolyte complex, and thereby increase loading efficiency of the agent, and improve the stability of the agent during the encapsulation process and subsequent release of the agent. In one embodiment, the polyelectrolyte complex comprises a positively charged glycosoaminoglycan that binds to one or more negatively charged loci on the protein or other macromolecular agent to be delivered from the system. Alternatively, in other embodiments, the polyelectrolyte complex comprises a negatively charged glycosaminoglycan that binds to one or more positively charged loci on the protein or other macromolecular agent to be delivered.

In some embodiments of the invention the biopolymer/macromolecule polyelectrolyte complex is present in the interconnected porous system of the microsphere as a nonsoluble polyelectrolyte complex, for example, as a coacervate and/or an amorphous precipitate, and therefore when bound in the polyelectrolyte complex, the macromolecule is inhibited from leaching out of the microsphere during self-healing encapsulation of the macromolecule.

The addition of a biopolymer to the inner water phase of the emulsion during microsphere formation can affect the interconnected pore structure of the microsphere. For example higher molecular weight HA (356 or 1010 kDa) has been shown to cause increasing viscosity of the inner water phase of the emulsion and at some HA concentrations, leads to poorly formed primary emulsions, which in turn, leads to deformed microspheres and non-uniform pore structure. In contrast, well-formed HA-PLGA microspheres have been obtained with 66 kDa HA at 2-13% w/w, indicating that both concentration and size of the biopolymer affect pore structure. Therefore, in one embodiment of the invention, values for the molecular weight of the biopolymer, the volume of the inner water phase, the PLGA concentration, microsphere size, trehalose loading, and $MgCO_3$ or other pH modifying species loading are selected to obtain well-formed microspheres having an interior space and interconnected pore network suitable to encapsulate and deliver the protein or other macromolecule of interest.

Ionic interactions govern the specificity of GAG-macromolecule binding and polyelectolyte complex formation. The polyelectrolyte complex may comprise either a positively charged biopolymer that binds to one or more negative loci of the protein or other negatively charged macromolecule, such as DNA, or siRNA. Alternatively, the polyelectrolyte complex may comprise a negatively charged biopolymer capable of binding to positively charged loci on the macromolecule agent to be delivered. For example, the carboxylate and sulfate groups of GAG's interact with the basic amino acid residues on a protein agent to provide optimal binding. Thus, the distribution and topology of the basic resides on the GAG dictates the strength and specificity of interactions with positively charged residues on the protein and the stability of the polyelectrolyte complex. In order to achieve strong binding affinity, oligosaccharide sequences on the GAG provide sulfate groups oriented on the surface of the molecule so that they are available for van der Waals-type interactions with basic amino acid residues on the protein agent. Therefore, the three-dimensional structure and conformation of the GAG plays a crucial role in protein binding. Residues of arginine, lysine and, to a lesser extent, histidine on the surface of the protein three-dimensional structure are involved in the ionic interactions with highly acidic sulfate groups present on the GAG chains. Binding is also affected by the size of the biopolymer-protein polyelectrolyte complex. In one embodiment of the invention, the interaction between the GAG (or other biopolymer) and the protein (or other agent) is strong enough to immobilize the agent, but also allow the biopolymer-agent polyelectrolyte complex to dissolve, and the agent to diffuse out of the delivery system as the polymer matrix degrades. In one embodiment of the invention, the binding constant ($k_a$) for the polyelectrolyte complex is in the range of $10^5$ to $10^7$.

In various embodiments, the biopolymer to be used in a biopolymer-PLGA delivery system is a GAG that is selected, based on its both its size and binding affinities for the protein agent to be delivered. In one embodiment of the invention, a nonsoluble polyelectrolyte complex forms between the biopolymer and a protein active agent during loading of the agent, is present in the pores of a self-healing polymer matrix, and because it is nonsoluble, restricting mobility of the protein, it does not substantially leach out during loading of the protein and stabilizes the structure of the protein.

In some embodiments of the invention, one or more GAGs are selected that stabilize the protein agent during the encapsulation process, increase loading of the protein agent into the porous biopolymer-PLGA microspheres, and release the protein agent under physiological conditions. In some embodiments of the invention, such a delivery system provides a means of delivering an active protein agent for an extended period of greater than 40 days. For example, in one embodiment of the invention, high molecular weight dextran sulfate (approximately 500 kDa) added to PLGA formulations were found to control release of lysozyme (LYZ) from the PLGA microspheres by reducing initial burst. In addition the rate of LYZ release could be adjusted by changing the HDS:protein ratio during encapsulation. Further, the high molecular weight of HDS minimizes potential leaching and complications during encapsulation of proteins, and results in high loading and encapsulation efficiency, and thereby reduces losses of expensive recombinant proteins during encapsulation. In one embodiment of the invention these encapsulation and release characteristics indicate that HDS-PLGA microspheres would be optimal for long-acting-release formulations.

Protein encapsulation by preformed porous PLGA microspheres is a two-step process consisting of a loading phase followed by pore closure, although some pore closing may occur during the loading phase and some loading may occur in the pore closure phase. Optimal encapsulation conditions require the lowest temperature and duration at which a majority of surface pores close while encapsulating the maximum amount of protein from the loading solution. In some embodiments of the invention, optimal results were achieved by incubating porous PLGA microspheres in protein agent solution for 48 h at 24° C. Healing is also beneficial to the polymer matrix after encapsulation because it allows the polymer chains to reach a lower energy state in contact with water, which should minimize physical aging of the polymer during storage. Physical aging can increase initial burst release. For example, when the polymer is initially hydrated before or during administration to a patient and exposure to injection vehicles and bodily fluids, the polymer would be less capable of an elastic response to incoming water, resulting in additional pore formation and burst release of the encapsulated active agent. A self healing polymer matrix can potentially be healed in numerous ways including external stimuli that result in mobilization of the surface polymer chains that causes them to undergo rearrangement to minimize the interfacial tension or other residual stresses in the polymer and thereby to heal the pore or defect. Healing could also be done in air if the T is raised above the relevant $T_g$ of the polymer, e.g., wet or dry $T_g$ depending on whether the polymer is hydrated or not.

One embodiment of the invention includes a method of making a delivery system for a macromolecule such as a protein, peptide, DNA, siRNA or other large molecules (i.e., roughly >1000 Da). First, using a double water-oil-water (W/O/W) emulsion, PLGA is formulated with one or more pore forming agents, a pH modulator such as $MgCO_3$ or $ZnCO_3$, and a biopolymer that is added to the inner water phase of the emulsion during microsphere formation and incorporated into the pores of the microsphere. The resulting porous microspheres have an interconnected pore network that will allow an active macromolecule agent that is to be delivered to penetrate deep into the interior of microsphere during encapsulation, and to diffuse out of the microsphere through the interconnected pore network at an optimal rate during subsequent controlled release. The biopolymer is selected to achieve sufficient binding affinity with the macromolecular agent to be encapsulated efficiently and/or to achieve other desired characteristics (high loading and/or improved protein stability, release, or activity). In addition, the molecular weight of the biopolymer, the volume of the inner water phase of the water-oil-water emulsion, the PLGA concentration, microsphere size, concentration of pore forming agent, and pH modifying agent loading are selected to obtain well-formed microspheres suitable to deliver the macromolecule of interest.

Next, the macromolecule is loaded into the preformed PLGA microspheres by incubating the microspheres in a solution of the macromolecule. The macromolecule diffuses into the microsphere where it binds to the biopolymer within the interior of the microsphere. Binding to the biopolymer immobilizes the macromolecular agent to be delivered, and thereby increases loading efficiency of the agent, and improves the stability of the agent during the encapsulation process and subsequent release of the macromolecular agent. The percent w/w load of the active agent is quantified as:

$$\left(\frac{\text{mass of protein encapsulated in microspheres}}{\text{total mass of microspheres in loading solution}}\right) \times 100.$$

The percentage encapsulation efficiency is calculated as:

$$\left(\frac{\text{mass of protein encapsulated in microspheres}}{\text{total mass of protein in loading solution}}\right) \times 100.$$

Finally, the loaded microspheres are incubated in an aqueous solution at a temperature above the $T_g$ so that the pores on the surface of the microsphere close (heal), encapsulating the macromolecule. In one embodiment PLGA microspheres have a hydrated glass transition temperature of well below 43° C., a temperature at which many macromolecules, including proteins are stable for sufficient periods of time to allow pore healing. However, in some embodiments, plasticizers are added to the PLGA to reduce the healing temperature to 37° C. Alternatively, in other embodiments different methods can be used to close the pores besides temperature change. For example, exposure to a solvent, such as alcohol vapor, can be used to facilitate pore closure (self-healing) of the polymer matrix. A self healing polymer matrix can potentially be healed in numerous other ways including external stimuli that result in mobilization of the surface polymer chains that causes them to undergo rearrangement to minimize the interfacial tension or other residual stresses in the polymer and thereby to heal the pore or defect. Healing could also be done in air if the T is raised above the relevant $T_g$ (wet or dry) of the polymer.

Loading the macromolecule into preformed microspheres and associating (binding) the macromolecule with a biopolymer within the microsphere, according to this method provides a delivery system exhibiting high loading and encapsulation efficiency of the macromolecular agent, a desirable release profile, and stability for an extended time period.

Various embodiments of the present invention are described in the examples below.

Example I

Porous PLGA microspheres, with a biopolymer (HA, HDS, CS, or HP) for protein absorption in the PLGA pores, $MgCO_3$ as a pH modulator, and trehalose to improve the pore structure of the microspheres were prepared by double water-oil-water (W/O/W) emulsion. The first emulsion was created by homogenizing 1 ml of 250 mg/ml PLGA (50/50 D,L lactic/glycolic ratio, lauryl ester end capped, 0.57 dL/g i.v.) and suspended $MgCO_3$ (~8.2 mg) in 1 mL $CHCl_3$ with an inner water phase of 200 microliters and containing ca. 8.2 mg trehalose and varying amounts of biopolymer, at 18000 rpm for 60 s over an ice bath, using the Tempest IQ2 (Vertis, USA). Two ml of 5% PVA solution was added to the resultant emulsion. The second emulsion was created by vortexing at 10,000 rpm for 60 s. The w/o/w emulsion was added to 100 ml of 0.5% PVA solution, and allowed to harden at room temperature for 3 h. Hardened microspheres (20-63 μm) were collected using sieves, washed with double-distilled water and immediately freeze dried.

Scanning electron microcopy (SEM) was used to verify that the microspheres were porous and well formed (spherical). Images were obtained using a Hitachi 53200N scanning electron microscope (Hitachi, Japan). Lyophilized microspheres were fixed on double-sided adhesive carbon tape. Samples were coated with a thin layer of gold (~5 nm) under vacuum and images were taken at 10-15 kV excitation voltage. EDAX software was used to obtain the final image.

LYZ (active protein agent) loading solutions were prepared in 10 mM phosphate buffer (pH 7) and FGF-20 loading solutions were prepared in 0.5 M arginine, 0.05 M sodium phosphate and 0.08% polysorbate 20 (pH 7). VEGF loading solutions were prepared in 5 mM succinate buffer, 275 mM trehalose and 0.01% polysorbate 20 (pH 5).

Pore closure was induced at 42.5° C. under mild agitation for 42 hrs. These parameters were determined by quantifying effect of temperature and duration of pore closure on lysozyme loading. BP-PLGA microspheres were removed from the loading solution, washed with double-distilled water, and immediately lyophilized. SEM images were taken to verify that a majority of surface pores had closed.

To quantify protein concentrations SE chromatography was performed using high pressure liquid chromatography (HPLC) and ultra-high pressure chromatography (UPLC) systems (Waters, USA). The mobile phase consisted of 0.1 M sodium phosphate with 0.3 M sodium sulfate at pH 6.7 at the rate of 0.8 ml/min and 0.4 ml/min for HPLC and UPLC, respectively. Samples and standards were injected onto TSKgel G2000SWxl (Tosoh Bioscience, USA) and Acquity BEH200 (Waters, USA) during HPLC and UPLC respectively. Protein detection by UV was done at 214 and 282 nm. Retention times of roughly 11 and 5 min were obtained for LYZ during HPLC and UPLC, respectively.

Example II

Biopolymer-PLGA microspheres were prepared using chondroitin sulfate (CS), high molecular weight dextran sulfate (HDS, approximately 500 kDa), low molecular weight dextran sulfate (LDS, approximately 15.5 kDa), and heparin (HP) according to the procedure of Example I. Biopolymer-PLGA microspheres containing 4% w/w biopolymer were loaded from 0.5, 1, and 1.5 mg/ml lysozyme (LYZ) solutions (Table 1). The biopolymer-PLGA microspheres exhibited excellent active protein loading capabilities and efficiency. LDS formulations had the lowest loading efficiencies (and corresponding LYZ loading) among the biopolymers tested. HDS, CS and HP formulations had greater than 90% efficiency across all loading concentrations investigated, and HDS-PLGA microspheres were found to have the highest loading efficiency. Most of the LYZ partitioned into the biopolymer containing PLGA pores when LYZ concentration in the loading solution increased from 0.5 mg/ml to 1 mg/ml and 1.5 mg/ml (Table 1). This high loading capacity (~7 wt %) and efficiency (94-96%) was achieved at a lower biopolymer:LYZ (in the loading solution) ratio. Loading was found to increase with the concentration of LYZ in the loading solution in the range investigated (FIG. 1). Thus, in one embodiment of the invention, the biopolymer concentration in the microsphere and the concentration of the protein agent in the loading solution can be adjusted to obtain microsphere formulations with a desired protein content.

TABLE 1

Encapsulation capacity and efficiency of Biopolymer-PLGA microspheres loaded from 1 ml LYZ solutions in 10 mM phosphate buffer (pH 7).

| BP | Loading Solution Conc. (mg/ml) | Lysozyme Loading | |
|---|---|---|---|
| | | % w/w | % Efficiency |
| HDS | 0.5 | 2.2 ± 0.1 | 90 ± 0.1 |
| HDS | 1 | 4.6 ± 0.1 | 95 ± 0.2 |
| HDS | 1.5 | 7.0 ± 0.1 | 97 ± 0.1 |
| LDS | 0.5 | 1.5 ± 0.1 | 63 ± 2 |
| LDS | 1 | 4.1 ± 0.1 | 83 ± 2 |
| LDS | 1.5 | 6.8 ± 0.2 | 91 ± 1 |
| CS | 0.5 | 2.1 ± 0.1 | 89 ± 0.1 |
| CS | 1 | 4.5 ± 0.1 | 95 ± 0.3 |
| CS | 1.5 | 7.4 ± 0.1 | 97 ± 0.2 |
| HP | 0.5 | 2.2 ± 0.1 | 90 ± 0.3 |
| HP | 1 | 4.7 ± 0.2 | 94 ± 1 |
| HP | 1.5 | 7.3 ± 0.1 | 97 ± 0.1 |

Example III

To determine the effect of biopolymer concentration (% w/w BP) on encapsulation efficiency, ~10 mg of HDS-PLGA (2, 5.1 and 12.6% w/w HDS) microspheres were loaded from 1 ml of 3 mg/ml and 0.5 ml of 6 mg/ml LYZ loading solutions (Table 2). A smaller amount of microspheres (~10 mg), were loaded with an excess of LYZ (3 mg) to further determine the role of loading solution concentration. Encapsulation was found to be higher at 6 mg/ml than at 3 mg/ml. The theoretical amount of LYZ bound to 1 mg of HDS increased with loading concentration. These data indicate that the maximum encapsulation capacity of HDS-PLGA microspheres increases with loading concentration of LYZ. Higher self-encapsulation was also seen with increasing HDS content, when loaded with an identical LYZ concentration (in the loading solution). Overall, the low loading and encapsulation efficiency could be attributed to the HDS-PLGA having exceeded the protein binding capacity, as a smaller mass of microspheres was loaded with higher amount of protein. Thus, the significance of loading solution concentration was verified at constant volume of LYZ loading solution and constant amount of LYZ in the loading solution.

TABLE 2

Encapsulation capacity and efficiency of HDS-PLGA microspheres loaded with an excess of LYZ from 10 mM phosphate buffer.

| | HDS | Loading Solution | | LYZ Loading | | LYZ bound |
|---|---|---|---|---|---|---|
| BP | (% w/w) | Vol. (ml) | Conc. (mg/ml) | (% w/w) | Efficiency | (mg/mg HDS) |
| HDS | 2 | 1 | 3 | 1.3 ± 0.1 | 4.5 ± 0.1 | 0.66 ± 0.01 |
| HDS | 5.1 | 1 | 3 | 3.4 ± 0.4 | 13.5 ± 0.4 | 0.67 ± 0.03 |
| HDS | 12.6 | 1 | 3 | 3.4 ± 0.3 | 13.1 ± 0.2 | 0.28 ± 0.02 |
| HDS | 2 | 0.5 | 6 | 4.1 ± 0.01 | 13.7 ± 0.1 | 2.03 ± 0.04 |
| HDS | 5.1 | 0.5 | 6 | 6.2 ± 0.3 | 20.9 ± 0.5 | 1.26 ± 0.02 |
| HDS | 12.6 | 0.5 | 6 | 8.1 ± 0.2 | 27.1 ± 0.3 | 0.67 ± 0.03 |

Example IV

Figure 2:
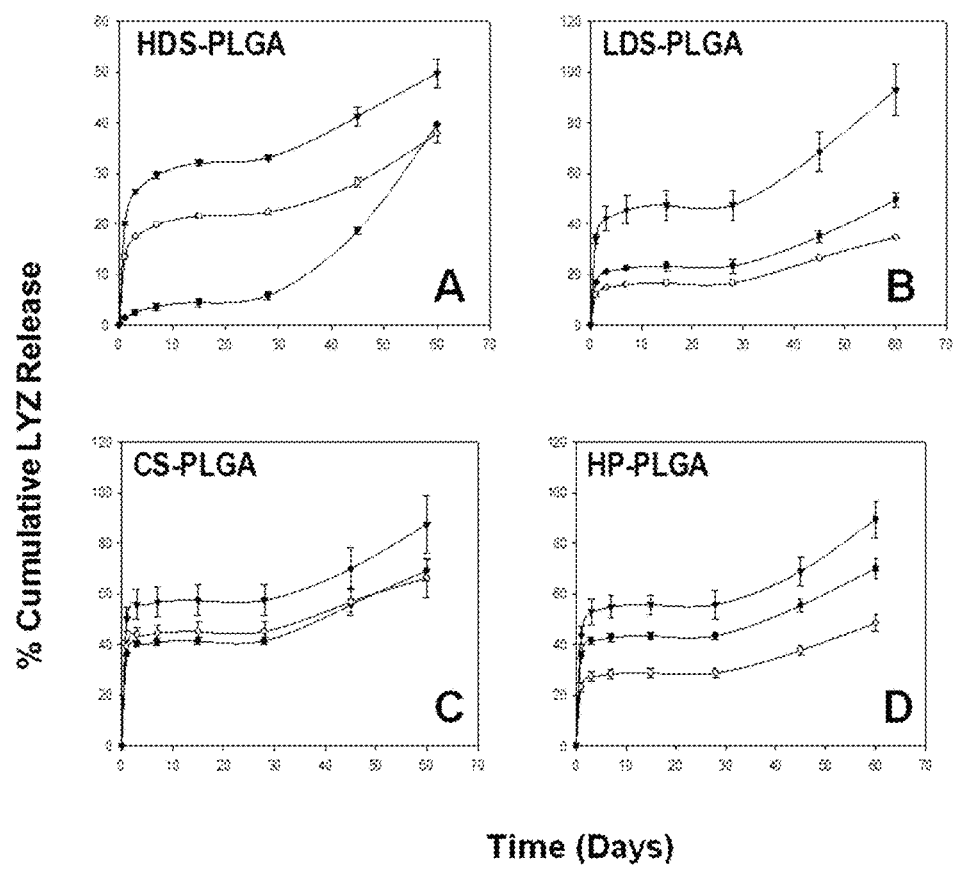
FIG. 2 is a graphical representation of lysozyme (LYZ) release profiles in 1 ml PBS (pH 7.4) at 37° C. quantified by SE-HPLC at 282 nm. Biopolymer-PLGA microspheres were loaded from LYZ in 10 mM phosphate buffer at concentrations of 0.5 (-●-), 1 (-○-) and 1.5 (-▼-) mg/ml. The values are expressed as mean±SD; n=3; total microsphere mass in release media was ~18 mg, in accordance with the present invention.

The release kinetics of encapsulated LYZ from sulfated biopolymer-PLGA microspheres was evaluated in 1 ml PBS at pH 7.4. For all formulations, the cumulative release plateaued at around day 7 and increased after 28 days of release (FIG. 2). The first stage (time 0 to about 3 days, FIG. 2A-D) of this two-phase release would be expected to be driven by diffusion of the LYZ, which was either poorly encapsulated or released from the microsphere prior to healing of newly formed pores created during drying or initial hydration of the microspheres. After this initial phase, continuous release was sustained by the presence of the $MgCO_3$ excipient, which reacts with the degradation products to create osmotic pressure and facilitating the opening of new pores in the polymer matrix. The kinetics is also likely governed by the biopolymer-LYZ interactions and the movement of complexed and soluble LYZ, through the pore network.

As shown in FIG. 2, biopolymer-PLGA microspheres loaded with 1.5 mg/ml LYZ had the highest rate of release and extent (≈80%) of release of the self-encapsulated LYZ. LDS-PLGA formulations also exhibited a higher rate and extent of release (FIG. 2-B) when compared to HDS (FIG. 2-A) loaded at 1.5 mg/ml LYZ. CS-PLGA formulations (FIG. 2-C) had the highest burst release (>40%) among the sulfated biopolymer-PLGA microspheres. Overall, HDS-PLGA microspheres had the lowest burst release, as well as most desirable rate and extent of long-term release among those formulations tested.

Example V

Figure 3:
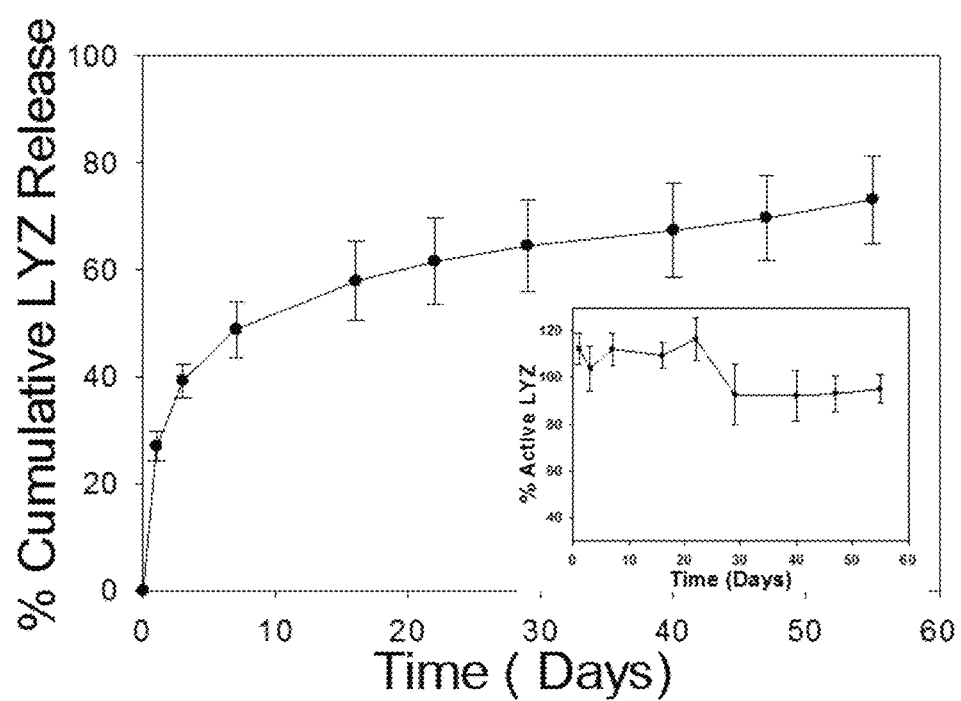
FIG. 3 is a graphical representation of LYZ release profiles in PBST (PBS with 0.02% Tween 80) quantified by SE-UPLC at 282 nm. HDS-PLGA microspheres were loaded from 1.5 mg/ml LYZ in 10 mM phosphate buffer (pH 7). The values are expressed as mean±SE; n=3; microsphere mass in solution was ~18 mg, in accordance with the present invention.

Approximately 18 mg of HDS-PLGA (loaded with 1.5 mg/ml LYZ) formulations were incubated in 5 ml PBST to evaluate LYZ release kinetics and activity of released LYZ (FIG. 3). The activity of LYZ in solution was determined by Enzchek® lysozyme assay (Life Technologies, USA) in accordance with the standard protocol provided by the company. HDS-PLGA formulations were found to have good release kinetics with ≈60% of the encapsulated LYZ released over 21 days (FIG. 3). The remaining LYZ was gradually released, leading to ≈73-80% of encapsulated protein being released over 55 days. The activity of the released LYZ was found be >90% during the entire course of release experiment (FIG. 3, Insert).

Example VI

Encapsulation of recombinant human fibroblast growth factor (FGF-20) and vascular endothelial growth factor 165 (VEGF165) was performed according to the method described in Example I. Theoretical content of $MgCO_3$, trehalose and biopolymer were ~3, 3, and 4% w/w in the formulations, respectively. Encapsulation of FgF-20 was from 1 ml of loading solution containing 0.5 mg/ml FGF-20 (0.5M arginine, 0.05 M sodium phosphate and 0.08% polysorbate). Encapsulation of VEGF in HDS-PLGA microspheres was from 1 ml of 1 mg/ml VEGF loading solution (5 mM succinate buffer, 275 mM trehalose and 0.01% polysorbate 20). Results are shown in Table 3.

Protein concentrations were determined by SE chromatography using ultra-high pressure chromatography (UPLC) systems (Waters, USA) as described in Example I. FgF-20 had a retention time of roughly 5 min during UPLC. VEGF had a similar retention time of roughly 5 min during UPLC. UPLC was preferentially used in quantifying protein release kinetics in 5 ml release media, as it had higher sensitivity when compared to SE-HPLC for the conditions studied.

VEGF was quantified using a Human VEGF standard ELISA development kit purchased from Peprotech (NJ, USA). Briefly, 96 well microplates were incubated overnight with 100 µl VEGF primary antibody at room temperature. After washing with PBS containing 0.05% polysorbate 20, 100 µl of standards and samples were added in triplicate and incubated for 2 h at room temperature. After washing with PBS containing 0.05% polysorbate 20, 100 µl of biotinylated secondary antibody was added to each well and allowed to incubate for 2 h at room temperature. After another wash with PBS containing 0.05% polysorbate 20, 100 µl of avidin-HPR conjugate was incubated in each well for 30 mins. After a final wash with PBS containing 0.05% polysorbate 20,100 µl of ABTS substrate was added to each well for detection. Activity was determined by monitoring plate optical density at 405 nm with wavelength correction set at 650 nm and fitting the data using the Gen5 software (Biotek, USA).

TABLE 3

Encapsulation of FGF-20 and VEGF-165; Mean ± SE, n = 3; total microsphere mass in loading solution was ~20 mg.

| BP | Loading Solution | Loading % (w/w) | % Efficiency |
|---|---|---|---|
| HDS | 0.5 mg/ml FgF-20 | 2.3 ± 0.1 | 87 ± 1 |
| LDS | 0.5 mg/ml FgF-20 | 2.1 ± 0.1 | 84 ± 1 |
| CS | 0.5 mg/ml FgF-20 | 1.9 ± 0.2 | 85 ± 2 |
| HP | 0.5 mg/ml FgF-20 | 2.1 ± 0.1 | 81 ± 1 |
| HDS | 1 mg/ml VEGF | 4.1 ± 0.4 | 73 ± 6 |

Loading efficiencies >80% with ~2% (w/w) were obtained for FgF-20, for all the formulations analyzed. Encapsulation was achieved in presence of 0.5 M Arg in loading solution to overcome solubility and stability issues associated with FgF-20. Upon encapsulation of VEGF165 by HDS-PLGA microspheres, ~4% (w/w) loading was obtained with nearly 75% efficiency. This was achieved in presence of 275 mM trehalose, to improve stability of the VEGF during the loading incubation.

Figure 4:
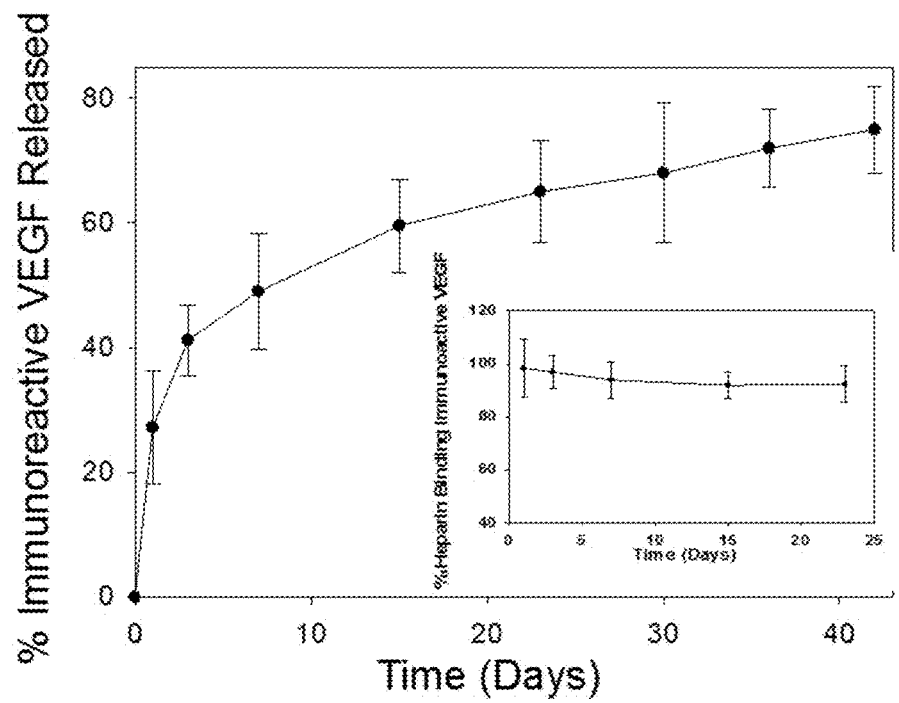
FIG. 4 is a graphical representation of a VEGF release profile from HDS-PLGA microspheres in 5 ml PBST (pH 7.4 with 1% BSA), quantified using ELISA. HDS-PLGA microspheres were loaded from 1 ml of 1.0 mg/ml VEGF solution (5 mM succinate buffer, 275 mM trehalose and 0.01% polysorbate 20, pH 7). The values are expressed as mean±SE; n=3, and total microsphere mass in release solution was ~18 mg. Insert—Heparin binding capacity of released VEGF was quantified using heparin-affinity chromatography and normalized VEGF concentration determined by ELISA, in accordance with the present invention.

The release kinetics of VEGF loaded HDS-PLGA was evaluated in 5 ml PBST+1% BSA, with full media replacement (FIG. 4). BSA was added in the release medium to improve stability of released VEGF and prevent non-specific adsorption to the release vessel. Over 42 days, nearly 72 of encapsulated VEGF was released in an immunoactive form. The VEGF released over a 40 day time period (FIG. 4) retained its ability to bind to heparin (>92% over 23 days, shown in Insert, FIG. 4), suggesting it retained its native tertiary structure. The release kinetics were found to be slightly faster when compared to LYZ, which could have resulted from the presence of 275 mM trehalose in the external loading solution, and reasonably could affect the VEGF-HDS interaction, and thus the binding and loading. Release kinetics of FgF-20 was not characterized because of the lack of a suitable release assay for a viable release media.

The approximate 4% w/w loading of VEGF achieved by the encapsulation method of the present invention is significantly higher than the prior art in which the VEGF was included in the first emulsion, during the preparation of PLGA particles. This is significant, as the present invention allows the protein to be loaded after the formation of the PLGA microparticle, protecting it from harsh conditions and processes associated with manufacturing that are known to cause degradation and loss of activity of proteins. LYZ release from PLGA has been shown to suffer from stability issues when encapsulated using methods known in the prior art. Using the methods of the present invention, high LYZ loading and encapsulation efficiency were achieved. In addition, an excellent release profile, and stability for a time period of 60 days were obtained. Thus, loading the protein or other macromolecule into preformed microspheres and associating (binding) the macromolecule with a biopolymer within the microsphere, according to the present invention provides a delivery system and method for long-acting release for delivery of proteins and other macromolecules.

Example VII

Preparation of Microspheres:

Microspheres were prepared using 50:50 PLGA, high molecular weight dextran sulfate (HDS) and zinc carbonate ($ZnCO_3$). Porous PLGA microspheres were made by water/oil/water emulsion solvent evaporation. 250 mg PLGA and 15 mg $ZnCO_3$ was dissolved in 1 ml $CH_2Cl_2$ by shaking for one hour. The inner water phase of 7.5 mg trehalose and 10 mg HDS was dissolved in 200 µl of histidine loading buffer then added to the PLGA-$ZnCO_3$ and homogenized at 18,000 rpm for one minute to form the o/w emulsion. The w/o/w emulsion was formed by adding 2 ml of 5% (w/v) PVA to the o/w phase, vortexing for one minute, then pouring the w/o/w emulsion into the hardening bath (0.5% w/v PVA) and stirring for three hours. When stirring was complete, microspheres were sieved between 20 and 90 µm, washed with water and freeze dried for two days.

Loading of Leptin into Microspheres:

Approximately 10 mg of microspheres were then incubated with 250 µl of leptin solution (2 mg/ml in 10 mM sodium acetate buffer pH 4) in 25° C. water bath for 48 hours. The leptin-loaded microspheres were then incubated at 43° C., with shaking, for 50 hours to close the pores (healing). Loaded, healed microspheres were washed with sodium acetate then freeze dried overnight. Encapsulation was determined by BCA protein assay of the supernatant and wash supernatant. Loading was found to be 3.69±0.55% w/w. Encapsulation efficiency was 73.58±1.18%.

Figure 5:
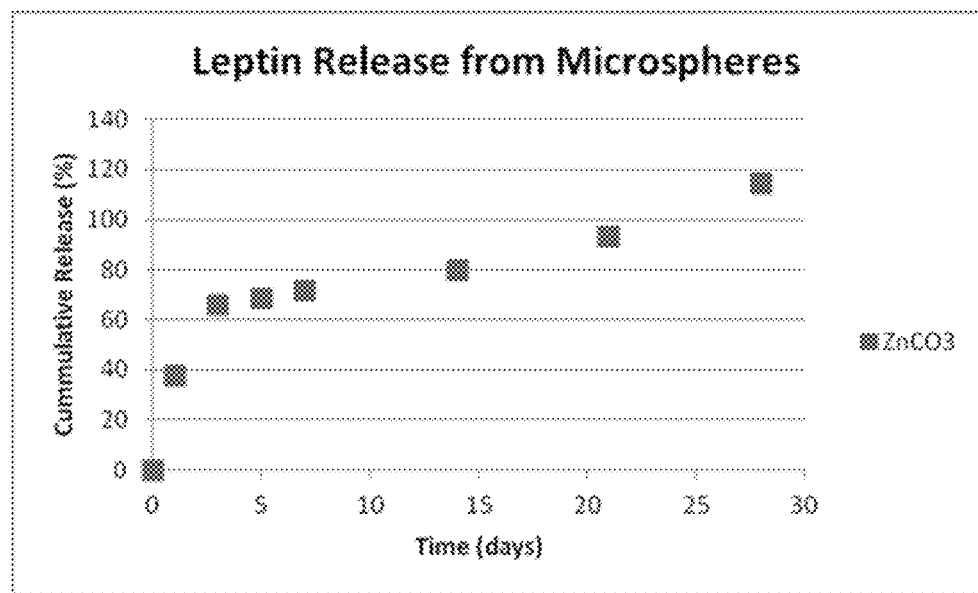
FIG. 5 is a graphical representation of a leptin release profile from $ZnCO_3$-PLGA microspheres, in accordance with the present invention.

Leptin Release Under Standardized Conditions:

Approximately 6 mg of leptin-loaded microspheres were re-suspended in release media comprising phosphate buffered saline-tween 80 (PBST-80), and maintained at 37° C. with mild shaking. At pre-determined time points the release medium was completely removed and replaced with fresh PBST-80, and analyzed by HPLC. In vitro slow, continuous release was observed for three weeks from the healed, biopolymer-PLGA microspheres, as shown in FIG. 5.

Example VIII

Self-healing microencapsulation of therapeutic anti-vascular endothelial growth factor (VEGF) monoclonal antibody (Fab fragment) in poly (D,L-lactic-co-glycolic acid) (PLGA) microspheres for treatment of wet age-related macular degeneration (AMD) was accomplished as follows.

Preparation of ASH-PLGA Microspheres:

Poly (D,L-lactic-co-glycolic acid) (PLGA, 50:50, MW=53.4 kDa, i.v.=0.60, end capped) microspheres were prepared by a double emulsion method. PLGA (250 mg) was dissolved in 1 mL of dichloromethane and poorly soluble bases ($MgCO_3$ or $ZnCO_3$) were added at 3% (weight/total particle weight) for MgCO3 and 6% for $ZnCO_3$ to prevent acid-induced instability of the encapsulated proteins and to provide continuous protein release. For the inner water phase, trehalose (3 w/w) and high molecular weight (ca. 500 kDa) dextran sulfate (HDS, 4% w/w) were added into 200 µL of 10 mM histidine buffer, pH 5.5 to create a percolating pore network in the polymer and to trap and stabilize the Fab during encapsulation, respectively. After homogenization (17000 rpm, 1 min) of this first emulsion, 2 mL of 5% PVA was added and vortexed for 1 min. The emulsion was poured into 100 mL of 0.5% PVA and stirred in hood. After evaporation of organic solvents, the hardened microspheres were collected by sieves (20-90 um) and followed by lyophilization.

Fab Fragment Loading:

The Fab fragment of commercially available bevacizumab was prepared with a Fab preparation kit (Thermo Scientific). Twenty milligram of ASH-PLGA Microspheres were suspended in Fab (1 mg, 0.5 mL of 2 mg/mL) solution in 10 mM histidine buffer, pH 5.5 in centrifuge tubes. They were incubated at 25° C. for 48 hrs for loading and then incubated at 43° C. for 50 hrs for pore closing. After incubation, the particles were washed three times with 1 mL of 10 mM histidine buffer, pH 5.5, then release study was performed in 6.66 mL of PBST+1% BSA. Loading percentage was determined by size exclusion-high performance liquid chromatography, as described in Example I.

Figure 6:
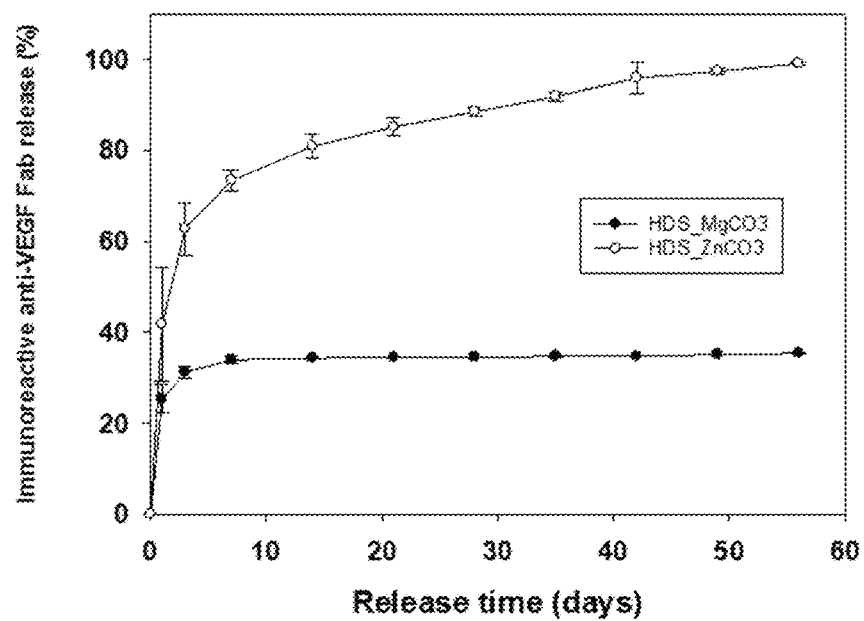
FIG. 6 is a graphical representation of a release profile of therapeutic anti-vascular endothelial growth factor (VEGF) monoclonal antibody Fab fragment from the $MgCO_3$-containing PLGA microspheres, (-●-) showing very low release after the initial burst (time 0 to day 10) and almost no release after day 14, with a total cumulative release of ~35% by day 56. Release from the weaker basic $ZnCO_3$-containing PLGA microspheres (-○-) was continuous after the burst, and continued during the whole release study period with a total cumulative release of ~99% by day 56, in accordance with the present invention.

Release of Fab Fragment Under Standardized Conditions:

In vitro release kinetics of immunoreactive Fab fragment from healed biopolymer-PLGA microspheres in PBS+ 0.02% Tween80+1% BSA at 37° C. was measured by enzyme-linked immunosorbent assay. The results are shown in FIG. 6. The initial burst release on day 1 ranged from 25-40%. Release from the $MgCO_3$-containing biopolymer-PLGA microspheres was very low after the burst, and almost stopped by day 14 with a total cumulative release of ~35% by day 28. By contrast, release from the weaker basic $ZnCO_3$-containing biopolymer-PLGA microspheres was continuous after the burst during the whole release study period with a total cumulative release of ~90% by day 28.

Advantages and Innovation:

Self-healing porous PLGA microspheres containing HDS and $ZnCO_3$ provide organic solvent-free encapsulation and long-term sustained release of immunoreactive anti-VEGF monoclonal antibody Fab fragment.

While the invention has been described with reference to particular embodiments it will be understood by one skilled in the art that variations and modifications may be made in form and detail without departing from the spirit and scope of the invention.

The invention claimed is:

1. A porous self-healing polymer matrix suitable for encapsulation of an active macromolecules selected from net positively charged peptides and net positively charged proteins, wherein the matrix comprises a biodegradable polymer and has pores and wherein:
   a biopolymer is disposed within the pores; and
   a pH modifying species is disposed within the pores;
   wherein the biopolymer comprises a dextran sulfate and is present at a level of greater than 0.5% and below 10% by weight based on the weight of the biodegradable polymer, and
   wherein the pH modifying species comprises magnesium carbonate and is present at a level of 1% to 7% by weight based on the weight of the biodegradable polymer.

2. The porous self-healing polymer matrix of claim 1 wherein the biodegradable polymer is selected from poly (lactides), poly(glycolides), poly(lactide-co-glycolides), poly(lactic-acid)s, poly(glycolic acid)s, poly(lactic acid-co-glycolic acid)s, poly(hydroxymethyl glycolide-co-lactide), polycaprolactone, polycarbonates, polyesteramides, polyanhydrides, poly(amino acids), polyorthoesters, polycyanoacrylates, poly(p-dioxanone), poly(alkylene oxalate)s, and polyurethanes.

3. The porous self-healing polymer matrix of claim 2 wherein the self-healing biodegradable polymer comprises poly(lactic-co-glycolic acid).

4. The porous self-healing polymer matrix of claim 1, wherein the porous self-healing polymer matrix is capable of sorbing at least 3.0% by weight of an active macromolecule, based on the final weight of the polymer matrix, from an active macromolecule loading solution having a concentration of 1 mg/mL.

5. The porous self-healing polymer matrix of claim 1, further comprising the active macromolecule encapsulated within the self-healing polymer matrix.

6. A method of using a porous self-healing polymer matrix for making a drug delivery system for an active macromolecule selected from net positively charged peptides and net positively charged proteins, the method comprising:
   loading the macromolecule into the porous self-healing polymer matrix according to claim 1 by incubating the self-healing polymer matrix in an aqueous solution of the macromolecule, wherein the matrix has pores connected to an outer surface of the matrix; and
   closing the pores and encapsulating the macromolecule.

7. The method of claim 6 wherein the dextran sulfate forms a non-soluble polyelectrolyte complex with the macromolecule to be delivered.

8. The method of claim 7 wherein the non-soluble polyelectrolyte complex stabilizes the structure of the macromolecule agent during the encapsulation process, and prevents the active macromolecule from leaching out of the porous polymer matrix.

9. The method of claim 6 wherein the loading of the active macromolecule is at least 3.0% w/w of the delivery system.

10. The method of claim 6 wherein the encapsulation efficiency of the active macromolecule is at least 60%.

* * * * *